United States Patent [19]

Neuwelt

[11] Patent Number: 5,059,415
[45] Date of Patent: Oct. 22, 1991

[54] METHOD FOR DIAGNOSTICALLY IMAGING LESIONS IN THE BRAIN INSIDE A BLOOD-BRAIN BARRIER

[75] Inventor: Edward A. Neuwelt, Portland, Oreg.

[73] Assignee: The State of Oregon Acting By and Through the Oregon State Board of Higher Education on Behalf of Oregon Health, Eugene, Oreg.

[21] Appl. No.: 314,940

[22] Filed: Feb. 21, 1989

[51] Int. Cl.$^5$ ..................... G01N 31/00; G01N 24/00
[52] U.S. Cl. ..................................... 424/9; 436/173; 436/806; 514/23
[58] Field of Search ................ 424/9; 436/173, 806; 128/653 F, 653 A, 654; 514/23

[56] References Cited

U.S. PATENT DOCUMENTS

| | | | |
|---|---|---|---|
| 4,331,647 | 5/1982 | Goldenberg | 424/1.1 |
| 4,479,932 | 10/1984 | Bodor | 424/9 |
| 4,540,564 | 9/1985 | Bodor | 424/9 |
| 4,735,210 | 5/1988 | Goldenberg | 128/654 |
| 4,764,598 | 8/1988 | Srivastava | 534/551 |
| 4,866,042 | 10/1989 | Neuwelt | 514/44 |
| 4,900,539 | 2/1990 | Goodman et al. | 424/1.1 |

OTHER PUBLICATIONS

Korguth, S. E. et al., J. Neurosurgery 66:698–906 (1987).
Barranger, J. A. et al., Modification of the Blood Brain Barrier: Increased Concentration & Fate of the Enzymes Entering the Brain Med. Sci 76(1):481–485 (1979).
Blasberg, R. G. et al., Regional Localization of a Glioma Associated Antigen Defined by Monoclonal Antibody, 81C6 in vivo Cancer Research 47:4432–4443 (1987).
Krejcarek, G. E. et al., Covalent Attachment of Chelating Groups to Macromolecules 77(2):581–585 (1977).
Hiesiger, E. M. et al., Opening the Blood Brain & Blood Tumor Barriers in Experimental Rat Brain Tumors Annimals of Neurology 19:50–59 (1986).

Primary Examiner—Glennon H. Hollrah
Assistant Examiner—Gary E. Hollinden
Attorney, Agent, or Firm—Klarquist, Sparkman, Campbell, Leigh & Whinston

[57] ABSTRACT

An improved method for diagnosing and characterizing brain lesions is described which first involves chemically modifying the blood-brain barrier (BBB) in order to increase BBB permeability. Thereafter, a chemical agent (e.g. monoclonal antibody) is introduced which binds directly, specifically and exclusively to brain lesons. The chemical has a label attached thereto (e.g. gadolinium-DTPA). The chemical agent and label localize in regions of brain lesion proliferation. Thereafter, the brain is quantitatively analyzed to determine the amount of labeling agent present, preferably using magnetic resonance imaging techniques. This procedure enables the accurate analysis of brain lesions, and represents an advance in the art of diagnostic imaging.

6 Claims, No Drawings

METHOD FOR DIAGNOSTICALLY IMAGING LESIONS IN THE BRAIN INSIDE A BLOOD-BRAIN BARRIER

This invention was made with Government support from the Veterans Administration, and under Grant No. 31770 awarded by the National Institutes of Health. The Government has certain rights in this invention.

BACKGROUND OF THE INVENTION

The present invention generally relates to a method for the diagnostic imaging of brain lesions, and more specifically to such a method in which labeled diagnostic agents are delivered across a chemically modified blood-brain barrier.

In diagnosing brain and central nervous system lesions, it is important to accurately characterize the type, size and extent of the lesions. This may be accomplished by the administration of chemical agents specific for lesion tissue which are labeled with appropriate diagnostic agents. However, materials used for this purpose are traditionally of high molecular weight and severely limited in their ability to penetrate the blood-brain barrier (BBB) of a patient. The BBB is a capillary barrier comprising a continuous layer of tightly bound endothelial cells. These cells permit a low degree of transendothelial transport, and exclude molecules in the blood from entering the brain on the basis of molecular weight and lipid solubility, as described in Neuwelt, E. A., "Is There a Therapeutic Role for Blood-Brain Barrier Disruption", *Ann. Intern. Med.* 93:137-139 (1980). For example, the BBB normally excludes molecules with a molecular weight greater than 180 daltons. In addition, the lipid solubility of molecules is a major controlling factor in BBB passage.

Considerable research has been conducted relating to the BBB and its permeability. Articles involving permeability of the BBB include:

1. "Chemotherapy of brain metastases: Current status", Greig, N. H., *Cancer Treatment Reviews*, 11:157-186 (1984).
2. "Cerebrovascular permeability and delivery of gentamicin to normal brain and experimental brain abscess in rats", Neuwelt, E. A., et al, *Journal of Neurosurgery*, 61:430-439 (1984).
3. "Blood-Brain Barrier: Phenomenon of Increasing Importance to the Imaging Clinician", Sage, M. R., *American Journal of Roentgenology*, 138:887-898 (1982).
4. "Opening the Blood-Brain and Blood-Tumor Barriers in Experimental Rat Brain Tumors: The Effect and Intracarotid Hyperosmolar Mannitol on Capillary Permeability and Blood Flow", Hiesinger, E. M. et al, *Annals of Neurology*, 19:50-59 (1986).

The foregoing articles discuss the permeability characteristics of the BBB in terms of lipid solubility, ionization fraction, protein binding and/or the molecular weight of foreign molecules. As specifically described by Sage, the function of the BBB is to maintain the homeostasis of the neuronal environment. The continuity produced by the tight junctions between individual cells of the BBB enables the cerebrocapillary endothelium to act like a plasma membrane. Small molecules (m.w. <200 daltons) having a high degree of lipid solubility and low ionization at physiological pH are freely passed through the BBB. In addition, the BBB allows water to move in either direction in order to maintain equal osmotic concentrations of solutes in the extracellular cerebral fluid.

However, recent research has shown that the BBB may become increasingly permeably during the development or onset of brain tumors, vascular lesions, or abscesses. As discussed by Sage, supra, the cerebrocapillary endothelium has a close investment by a glial sheath. Destruction of the glial sheath by mitotic activity may make the capillaries therein more permeable. Tumors appear to stimulate the proliferation of abnormal capillaries by releasing specific angiogenic factors in the brain.

The unique biological aspect of the BBB is an important focus in treating central nervous system disorders. While the interendothelial junctions between the cells of the BBB are normally designed to keep potentially noxious substances away from the brain, this condition changes during the formation of brain abscesses, inflammation, and/or tumors, as described above. For example, tests have shown that experimental allergic encephalomyelitis (EAE) may cause an immune reaction which increases the permeability of the BBB. Alvoode, E. C. et al, "Experimental Allergic Encephalomyelitis: A Useful Model For Multiple Sclerosis", *Prog. Clin. Biol. Res.*, Vol. 146, Alan, R., Liss Co., N.Y. 1984. One explanation for the increased permeability of the BBB at the onset of EAE involves the capability of endothelial cells of the cerebrovasculature system to act as antigen present cells (APCs), thus attracting T-cells and aiding their penetration across the BBB. Accordingly, it has been found that brain endothelial cells are capable of expressing histocompatibility antigens on their surfaces.

Another possible explanation for the increase in permeability of the BBB during the onset of lesions involves the ability of the brain under these circumstances to generate vasoactive substances, as described in Black, K. L., "Leukotrienes Increase Blood-Brain Barrier Permeability Following Intraparenchymal Injections In Rats", *Ann. Neurol.*, 18:349-351 (1985). Brain lips are rich in arachidonic acid which may be released by trauma to the brain tissue, e.g., by neoplastic invasion or ischemia. Black has shown experimentally that arachidonic acid and leukotrienes can increase BBB permeability when injected directly into the rat brain. Leukotriene content of the brain tissue correlates significantly with the amount of edema surrounding various CNS neoplasms, and it is conceivable that leukotrienes released from the damaged brain contribute to BBB disruption and vasogenic edema in CNS neoplasia.

Likewise, inflammation of brain tissue in immune-mediated CNS disease might possibly cause release of arachidonic acid and leukotrienes which would increase the permeability of the BBB. A further discussion of increased BBB permeability with reference to nervous system disorders, including infections, inflammatory conditions, neoplasms, and ischemia is presented in Fishman, R. A., *Cerebrospinal Fluid in Diseases of the Nervous System*, W. B. Saunders Co., Philadelphia, London, Toronto, 1980; Tourtelotte, W. "On Cerebrospinal IgG Quotients In Multiple Sclerosis and Other Diseases. A Review And A New Formula To Estimate The Amount of IgG Synthesized Per Day By the Central Nervous System", *J. Neurol. Sci.*, 10:279-304 (1970).

With respect to the diagnosis of brain lesions, a variety of different techniques have been attempted. However, most of them encounter problems associated with the delivery of diagnostic imaging agents across the BBB. For example, one diagnostic procedure involves CT (computed tomography) scanning using a meglumine iothalamate imaging agent. Tests using this procedure have shown that meglumine iothalamate has difficulty passing through the BBB, and exhibits a high degree of neurotoxicity. In addition, this method is associated with an unacceptable degree of seizures in clinical trials as described in Neuwelt, E. A., et al, "Osmotic Blood Brain Barrier Modification: Clinical Documentation by Enhanced CT Scanning and/or Radionuclide Brain Scanning", *Am. J. Neuroradiol.*, 4:907–913 (1983).

Another diagnostic method involves standard radionuclide imaging. This procedure is characterized by poor spatial resolution, and an inability to accurately image specific structures and regions in the brain. Also, time constraints exist when this method is used because of the short half-life of most radionuclides. For example $^{99m}TC$ is commonly used which has a half-life of about six hours.

Problems involving the accurate determination of brain lesion size are also present in other diagnosis methods including a recently perfected technique known as SPECT (single photon emission computerized tomography). Thus, a need currently exists for an improved method of diagnosing and characterizing brain lesions which avoids the problems described above, including impermeability of the BBB to diagnostic imaging agents. The present invention satisfies this need, as described herein.

SUMMARY OF THE INVENTION

It is an object of the present invention to provide a method for diagnosing and characterizing brain lesions.

It is another object of the invention to provide a method for diagnosing and characterizing brain lesions which is highly accurate and readily enables the determination of brain lesion size.

It is a further object of the present invention to provide a method for diagnosing and characterizing brain lesions which facilitates the passage of diagnostic imaging agents into the brain using BBB modification techniques.

It is an even further object of the present invention to provide a method for diagnosing and characterizing brain lesions which incorporates the use of labeled molecules biologically specific for brain lesion tissues which enables accurate lesion size determination.

In accordance with the foregoing objects, an improved method for diagnosing and characterizing brain lesions is disclosed. The method involves chemical modification of the BBB using mannitol or the like to increase BBB permeability. Thereafter, a chemical agent is introduced which is biologically specific for brain lesion tissues (e.g. a monoclonal antibody). This agent includes a diagnostic label, with gadolinium-DTPA being preferred. Upon administration, the labeled agent localizes the regions of brain lesion proliferation. Thereafter, the brain is analyzed to determine how much labeled material remains, preferably using magnetic resonance imaging techniques. Use of this procedure enables accurate quantitative information to be obtained regarding brain lesions, and represents an advance in the art of diagnostic medical imaging.

These and other objects, features and advantages of the invention will be described below in the following detailed description of a preferred embodiment and Example.

DETAILED DESCRIPTION OF A PREFERRED EMBODIMENT

The present invention represents an improved diagnostic imaging procedure for determining the size and character of brain lesions. The term "brain lesions" as used herein shall encompass malignant tumors, CNS infections, brain abscesses, cerebro-vascular disorders, and even degenerative disorders such as Parkinson's disease and Alzheimer's disease. These disorders have many causes, including bacterial/viral infections or problems of genetic origin.

As previously described, conventional brain lesion imaging methods are characterized by numerous problems, including substantial impermeability of the blood-brain barrier (BBB) to the diagnostic imaging agents. In accordance with the present invention, a method is provided which overcomes this problem and permits the delivery of labeled molecules across the BBB which are used as diagnostic imaging agents, as described below.

Initially, a chemical agent designed to increase the permeability of the BBB is administered. Exemplary materials for this purpose include hypertonic solutions of mannitol, arabinose, and/or glycerol. Chemical disruption of the BBB in this manner has been described in a variety of articles, including Neuwelt, E. A. et al, "Osmotic Blood-Brain Barrier Opening to IgM Monoclonal Antibody in the Rat", *Am. J. Physiol.*, 250:R875–883 (1986).

By chemically disrupting the BBB, large molecules have been transferred into the brain tissues of animal subjects. For example, in Neuwelt, E. A. et al, "Osmotic Blood-Brain Barrier Opening to IgM Monoclonal Antibody in the Rat", supra, monoclonal antibodies Ab348 624E5 and Ab350 624H12 (both rat immunoglobin IgM) were administered to adult Sprague-Dawley rats after the administration of mannitol solutions. Osmotic BBB opening in the rats significantly increased monoclonal antibody uptake into the rat brain tissues.

Administration of the BBB-modifying chemicals in the present invention is generally accomplished by intra-arterial infusion techniques known in the art. As a result, BBB permeability is greatly increased. For example, a normal, unmodified BBB will prevent molecules larger than 180 daltons from entering the brain. After the administration of suitable agents, the BBB will permit molecules having a molecular weight of 1,000,000 daltons to pass.

Subsequent to BBB modification, a second chemical agent is administered which binds specifically and exclusively to lesion tissues. Exemplary agents usable in the invention for this purpose include monoclonal antibodies or other lesion-specific proteins such as enzymes or agents that react with unique cell surface antigens. The specific chemical agents to be used will vary in accordance with the type of lesion involved. One example of a tissue-specific monoclonal antibody is described in Kornguth S., et al, "Magnetic Resonance Imaging of Gadolium-Labeled Monoclonal Antibody Polymers Directed at Human T-Lymphocytes Implanted in Canine Brain", *J. Neurosurg.*, 66:898–906 (1987). In this article, an intracerebral lesion was created by the implantation of human T lymphocytes in canine brain tissues. Gadolium-labeled monoclonal antibodies specific for human T lymphocytes were used as lesion-specific testing agents. The gadolinium-labelled antibodies were clearly localized to the injected lymphocytes when administered following osmotic BBB modification. While Kornguth et al. involves the labelling of normal tissue cells (e.g. human T lymphocytes), the present invention is entirely different. Specifically, it involves the use of chemical agents specific for lesion tissues (abnormal tissues), and binds directly and exclusively to those tissues.

The selected chemical agent is labeled prior to administration so that the agent may be subsequently detected. Preferred labeling materials include paramagnetic substances such as nitroxyl stable free radicals, transition elements, rare-earth elements ($Gd^{+3}$, $Mn^{+2}$) and molecular oxygen, with gadolinium-DTPA being preferred. The use of gadolinium-DTPA as an imaging agent is generally described in Brasch, R. G., et al, "Contrast-Enhanced NMR Imaging: Animal Study Using Gadolinium-DTPA Complex," *American Journal of Radiology*, 142:625-630 (1984); and Weinmann, H. J., et al, "Characteristics of Gadolinium-DTPA Complex: A Potential NMR Contrast Agent," *American Journal of Radiology*, 142:619-624 (1984).

A gadolinium-DTPA labeling material suitable for use as discussed herein is available from Berlex Laboratories of Wayne, N.J., and is preferably manufactured by dissolving gadolinium chloride in a 0.1 M citrate buffer (pH 5.8) to obtain a 0.1 M gadolinium chloride solution. Solid undissolved DTPA (diethylenetriamine pentaacetic acid) in an equimolar ratio to gadolinium chloride is then added to the gadolinium chloride solution, followed by incubation of the mixture at room temperature for about 30 minutes to obtain 0.1 M solution of gadolinium-DTPA. Each DTPA molecule will bind two molecules of gadolinium. The dissociation constant of the resulting complex is very high ($10^{-20}$), thereby indicating that all of the gadolinium is bound to DTPA. The DTPA in this complex serves primarily as a metal chelator and protein cross-linking agent. Gadolinium materials are highly effective labeling agents as previously described, and discussed in Runge, V. M., et al, "Contrast Enhanced MRI Evaluation of a Canine Model of Osmotic Blood-Brain Barrier Disruption," *Invest Radiol.*, 20:830-844 (1985); Unger, E. C., et al, "Magnetic Resonance Imaging Using Gadolinium Labelled Monoclonal Antibody," *Invest Radiol.*, 20:693-699 (1985); Anderson-Berg, W. T., et al, "Nuclear Magnetic Resonance and Gamma Camera Tumor Imaging Using Gadolinium-Labelled Monoclonal Antibodies, " *J. Nucl. Med.*, 27:829-833 (1986); and Korngruth, S. E., et al, "Magnetic Resonance Imaging of Gadolium-Labeled Monoclonal Antibody Polymers Directed at Human T-Lymphocytes Implanted in Canine Brain," supra. However, the labeling materials described herein (including gadolinium-DTPA) are attached directly to lesion-specific agents (e.g. monoclonal antibodies) designed for passage through the BBB. Attachment of the labeling materials may be accomplished using known methods generally described in, for example, Krejcarek, G. E., et al, "Covalent Attachment of Chelating Groups to Macromolecules, " *Biochem. & Biophys. Research Comm.* 77:581-585 (1977). This article specifically involves the attachment of DTPA to proteins. By way of example, the article discusses attachment of DTPA to albumin. Specifically, DTPA (0.1 gm, 0.25 mmoles) and triethylamine (0.125 gm, 1.25 mmoles) were dissolved in 2 ml $H_2O$ with gentle heating. The resulting solution was then lyophilized to yield a glassy residue. The residue (pentatriethylammonium DTPA) was then dissolved in 2 ml of acetonitrile with gentle heating. The solution was then cooled in an ice bath, and isobutylchloroformate (0.035 gm, 0.025 mmoles) added thereafter. This combination of materials was continuously stirred followed by cooling in an ice bath for 0.5 hours, which resulted in the precipitation of triethylamine hydrochloride. The resulting mixed carboxycarbonic anhydride of DTPA was then added to a cooled solution containing 0.25 gm HSA (human serum albumin) and 20 ml of 0.1 M sodium bicarbonate. As the DTPA solution was added, the pH was adjusted with the 0.1 M sodium bicarbonate, maintaining a pH of between 7-8. The reaction mixture was then placed in a refrigerator at 4° C. overnight and subsequently dialyzed against 0.1 M acetate buffer (pH 5.0). The desired protein fraction was isolated by gel chromatography on Sephadex G-25. Fractions corresponding to DTPA-HSA were combined and dialyzed against 0.1 M glycine HCL buffer (pH 3.5). Exhaustive dialysis and gel chromatography were necessary in order to remove excess DTPA not covalently attached to the HSA.

While the foregoing method specifically describes the formation of one chelated complex, it is equally applicable to the formation of a variety of different materials, including those usable in the present invention.

After production of the labeled complex, it is administered to a subject (preferably by intra-arterial infusion techniques), followed by localization in lesion tissue. Any excess material not bound to lesion tissue is allowed to be removed from the body by renal clearance or elimination of feces.

Next, detection of the labeled material is undertaken preferably using magnetic resonance imaging techniques. Magnetic resonance imaging is a relatively new diagnostic procedure, as generally described in Bradley, R. G, et al, "Comparison of CT and MR in 400 Patients with Suspected Diseases of the Brain and Cervical Spinal Cord," *Radiology*, 152:695-702 (1984); and Hesselink, J. R., et al, "MR Contrast Enhancement of Intracranial Lesions with Gd-DTPA," *Radiol. Clin. North Am.*, 26:873-887 (1988). In general, hydrogen density, and flow ($T_1$ and $T_2$) are the parameters which are measured in magnetic resonance imaging ($T_1$=spin-lattice or longitudinal relaxation time; $T_2$=spin-spin or transverse relaxation time). Both $T_1$ and $T_2$ are inherent magnetic properties of the tissue being scanned. This contrasts with CT scanning where electron density and effective atomic number are the physical properties which are measured. CT techniques can adequately image the axial plane of brain tissues, but reconstructions of the coronal and sagittal planes of the brain show markedly inferior spatial resolution. A typical magnetic resonance imaging system usable in accordance with the invention is a Sigma MR Scanner unit sold by the General Electric Co., of Milwaukee, Wis.

Diagnostic analysis using magnetic resonance imaging in conjunction with a labeled agent enables accurate images to be obtained in the coronal, axial, and sagittal planes of the brain without undesired ionizing radiation. Magnetic resonance imaging with gadolinium-DTPA yields highly accurate anatomic and quantitative information regarding brain lesions.

The following Example discusses specific tests conducted using magnetic resonance imaging techniques in connection with a lesion-specific agent having a gadolinium-DTPA label.

EXAMPLE

Research has indicated that a paramagnetic material (gadolinium-DTPA) can be delivered across the BBB utilizing barrier modification. Monitoring was accomplished using magnetic resonance imaging incorporating a 1.5 Tesla magnet. At times ranging from 0.5-14 3 hours after the administration of 0.15 and 0.20 mmole/kg of gadolinium-DTPA, clear increased signals have been documented on $T_1$ weighted images. Lower dosages such as 0.01 mmole/kg were not sufficient to demonstrate any change in the signal from the MRI imaging. At more intermediate doses of 0.05 mmole/kg, a change in signal was detected at a very early point in time (30 minutes) but not after 3 hours. However, preliminary studies indicate that 0.10 mmole/kg Gd-DTPA given with barrier modification results in unacceptable neurotoxicity while 0.05 mmole/kg Gd-DTPA may be well tolerated.

Gadolinium-DTPA may be combined with a variety of different monoclonal antibodies, depending on the type of lesions involved. Standard techniques as discussed above may be used to form the antibody-DTPA complex.

Use of the general method described herein enables a high degree of tumor resolution to be attained. Current imaging techniques are incapable of accurately identifying the histology of a tumor/lesion. It is not even possible to differentiate primary from metastic tumors based on current techniques including CT scanning, and angiography. Thus, by utilizing magnetic resonance imaging scanning, in combination with an antibody-label complex, a substantial advance in the diagnosis of brain lesions is achieved. Furthermore, the present invention may eliminate the need for neuro-surgical operations (e.g. biopsy procedures) in the diagnosis of lesions. The lesions may also be analyzed specifically by cell type so that different cancer metastasis forms may be differentiated with a high degree of accuracy. This is accomplished by combining the specificity of the lesion-specific agents with a high degree of spacial resolution characteristic of magnetic resonance imaging.

Having herein described a preferred embodiment of the invention, it is anticipated that suitable modifications may be made by those skilled in the art. For example, the lesion binding agents, labels, and BBB-modifying drugs may all be suitably varied provided they function in the manner described herein. Thus, the scope of the invention shall only be construed in accordance with the following claims:

What is claimed is:

1. A method for diagnostically imaging a naturally occurring brain lesion in a warm-blooded animal having a brain situated inside a blood-brain barrier having an ambient permeability level, the method comprising the steps:
   administering a first chemical agent to said animal at a location outside the blood-brain barrier, where the first chemical agent is capable of increasing the permeability of the blood-brain barrier from the ambient level to an elevated permeability level;
   administering a second chemical agent to said animal at a location outside the blood-brain barrier following the administration of said first chemical agent, said second chemical agent being capable of binding preferentially to a naturally occurring brain lesion and of passing through the animal's blood-brain barrier to the brain lesion when the blood-brain barrier is at the elevated permeability level but not at the ambient permeability level, said second chemical agent comprised of molecules having at least one labeling agent attached to each said molecule;
   allowing the animal to eliminate any amount of the second chemical agent with attached labeling agent not bound to said brain lesion; and
   analyzing said brain of said animal for the presence of said labeling agent bound to the brain lesion in order to determine the size, type, and character of said brain lesion.

2. The method of claim 1 wherein said first chemical agent comprises a material selected from the group consisting of mannitol, arabinose, and glycerol.

3. The method of claim 1 wherein said second chemical agent comprises a monoclonal antibody.

4. The method of claim 1 wherein said labeling agent comprises gadolinium-DTPA.

5. The method of claim 4 wherein the step of analyzing said brain of said animal for the presence of said labeling agent comprises conducting a magnetic resonance imaging scan of said brain.

6. A method for diagnostically imaging a naturally occurring brain lesion in a warm-blooded animal having a blood-brain barrier having an ambient permeability level, the method comprising the steps of:
   administering a first chemical agent to said animal at a location outside the blood-brain barrier, where the first chemical agent is capable of increasing the permeability of the blood-brain barrier from the ambient level to an elevated permeability level and comprises a hypertonic solution of a material selected from the group consisting of mannitol, arabinose, and glycerol;
   administering a second chemical agent to said animal at a location outside the blood-brain barrier following administration of said first chemical agent, said second chemical agent being capable of binding preferentially to a naturally occurring brain lesion tissues and of passing through the animal's blood-brain barrier to the brain lesion when the blood-brain barrier is at the elevated permeability level but not at the ambient permeability level, where said second chemical agent comprises monoclonal antibody molecules each having at least one labeling agent comprising gadolinium-DTPA attached to each said monoclonal antibody molecule;
   allowing the animal to eliminate any amount of the second chemical agent with attached labeling agent not bound to said brain lesion; and
   analyzing said brain of said animal for the presence of said labeling agent bound to the brain lesion in order to determine the size, type, and character of said brain lesion, said analyzing comprising the step of conducting a magnetic resonance imaging scan of said brain.

* * * * *

UNITED STATES PATENT AND TRADEMARK OFFICE
CERTIFICATE OF CORRECTION

PATENT NO. : 5,059,415

DATED : October 22, 1991

INVENTOR(S) : EDWARD A. NEUWELT

It is certified that error appears in the above-identified patent and that said Letters Patent is hereby corrected as shown below:

Title page item [73]: the Assignee should be --The State of Oregon Acting By and Through the Oregon State Board of Higher Education on Behalf of Oregon Health Sciences University, Eugene, Oregon--.

Title page item [56] under Other Publications, in the last paper cited, "Annimals" should be --Annals--.

Column 2, line 5, "permeably" should be --permeable--.

Column 2, line 7, "supra" should be --supra--.

Column 2, line 41, "lips" should be --lipids--.

Column 3, line 20, "$^{99m}TC$" should be --$^{99m}Tc$--.

Column 4, line 37, "supra" should be --supra--.

Column 5, line 5, "normal" should be --normal--.

Column 5, line 8, "abnormal" should be --abnormal--.

Column 5, line 33, after "obtain" add --a--.

Column 5, line 52, "Gadolium-Labeled" should be --Gadolinium-Labelled--.

Column 5, line 54, "supra" should be --supra--.

Column 7, line 7, "0.5-14 3" should be --0.5-3--.

UNITED STATES PATENT AND TRADEMARK OFFICE
CERTIFICATE OF CORRECTION

PATENT NO. : 5,059,415

DATED : October 22, 1991

INVENTOR(S) : EDWARD A. NEUWELT

It is certified that error appears in the above-identified patent and that said Letters Patent is hereby corrected as shown below:

Column 8, line 46, delete "tissues".

Signed and Sealed this

Fifth Day of May, 1992

Attest:

*Attesting Officer*

DOUGLAS B. COMER

*Acting Commissioner of Patents and Trademarks*